United States Patent [19]
Gauthier

[11] Patent Number: 6,122,065
[45] Date of Patent: Sep. 19, 2000

[54] APPARATUS AND METHOD FOR DETECTING SURFACE DEFECTS

[75] Inventor: Pierre Gauthier, Boisbriand, Canada

[73] Assignee: Centre de Recherche Industrielle du Quebec, Ste-Foy, Canada

[21] Appl. No.: 08/689,393

[22] Filed: Aug. 12, 1996

[51] Int. Cl.⁷ .................................................. G01B 11/00
[52] U.S. Cl. .......................... 356/394; 356/391; 356/376; 356/371
[58] Field of Search .................................... 356/391, 376, 356/371, 237, 394

[56] References Cited

U.S. PATENT DOCUMENTS

| | | |
|---|---|---|
| 4,162,126 | 7/1979 | Nakagawa et al. . |
| 4,277,803 | 7/1981 | Sano . |
| 4,827,142 | 5/1989 | Hatje . |
| 4,847,510 | 7/1989 | Douglas ................................. 250/560 |
| 5,083,867 | 1/1992 | Burk . |
| 5,085,516 | 2/1992 | Bertrand et al. ......................... 356/394 |
| 5,177,556 | 1/1993 | Rioux . |
| 5,229,835 | 7/1993 | Reinsch . |

FOREIGN PATENT DOCUMENTS

| | | |
|---|---|---|
| 0 692 714 A1 | 7/1995 | European Pat. Off. . |
| WO 89/08836 | 9/1989 | WIPO . |
| WO 95/24636 | 9/1995 | WIPO . |

*Primary Examiner*—Frank G. Font
*Assistant Examiner*—Reginald A. Ratliff
*Attorney, Agent, or Firm*—James Anglehart; Swabey Ogilvy Renault

[57] ABSTRACT

Apparatus and method for detecting surface defects on an article freely standing on a conveyer, which generate profile trace data corresponding to profile trace at a cross-section of the article. A surface shape inspection unit comprising an optical ranging system using laser and camera is provided for obtaining the profile trace data through triangulation-based derivation techniques. Base reference curves are derived from regular portions of the profile trace data. Profile trace data are compared to defect threshold curves to recognize a defect induced departure of the trace data with respect to the base reference curve and to produce a defect output signal. The apparatus and method according to the invention are particularly useful for detecting roughness, cavities, wane, missing wood and altered wood on lumber pieces which are conveyed at high speed.

40 Claims, 8 Drawing Sheets

APPARATUS AND METHOD FOR DETECTING SURFACE DEFECTS

FIELD OF THE INVENTION

The present invention relates to the field of surface defects detection, and more particularly to optical apparatus and method for non-contact detection of exposed defects on the surface of articles while carried by a transport device such as a mechanical conveyor.

DESCRIPTION OF THE PRIOR ART

In the past years, many systems have been proposed for detecting surface defects on articles for sorting or processing operations that were conventionally performed by human visual inspection. Such systems are particularly useful in manufacturing lines for improving production rate and product quality. An example of prior art system for optically testing sawed timber for faults is disclosed in U.S. Pat. No. 4,827,142, issued on May 2, 1989 to Hatje, which system uses a light source directing a beam of light in a plane at right angle to a longitudinal direction on the timber, for performing a line scanning of a transverse portion of the timber surface. A conveyor is provided for moving and guiding a timber in the longitudinal direction for lengthwise inspection. An optical detection device located in the light source plane is provided for detecting faults in the timber through brightness changes of the light beam reflected from the illuminated portion, to generate information signals in response to these brightness changes. A computer receiving the information signals derives respective positions of faults on the timber for storing thereof in a computer memory. With such a prior art system employing right angle illumination, applications are generally limited to detection of visible surface defects showing characteristic defective zones contrasting with adjacent surface areas, such as knots, roots or red rots, causing detectable brightness changes of the reflected light beam, without providing any specific indication on the type of defect involved. Moreover, where applications require detection of geometrical surface defects such as wane, holes, roughness or missing wood zones, right angle illumination is generally inadequate.

In U.S. Pat. No. 5,229,835, issued on Jul. 20, 1993 to Reinsch, an optical monitoring apparatus for measuring roughness of a surface is described, which comprises an optical source sending a scanning optical beam at an acute angle toward a surface for which roughness is to be monitored. Reflected light is caused to reach an optical sensor producing an output signal having a fluctuating configuration essentially matching the profile of the scanned surface. Following an amplifying stage, a resulting signal is fed in parallel to amplitude and spatial frequency analyzing devices. The amplitude analyzing device generates an output signal whose amplitude is an average of the RMS value of amplitude variations of the resulting signal, which output signal represents height of the bumps on the surface. On the other hand, the spatial frequency analyzing device generates an output signal whose magnitude is an average of the spatial frequency characterizing distance between the bumps on the surface. A processing circuit is provided for deriving from amplitude and frequency signals a quantitative measure of the surface roughness. However, such apparatus does not have capabilities for detection and dimensional measurements of localized geometrical surface defects such as wane and cavities in lumber.

In U.S. Pat. No. 4,162,126 issued on Jul. 24, 1979 to Nakagawa et al., there is disclosed a testing apparatus that can classify and evaluate defects on a surface of an object, such as broken cavities, cracks and pinholes. The apparatus comprises illumination sources for directing collimated light rays onto the surface of the object from at least two opposed and oblique directions, and a light sensor responsive to diffused light reflected by the surface in a perpendicular direction thereof, for producing a sensed signal corresponding to a surface condition measurement. According to a first detection function, the sensed signal is discriminated by a first threshold level that is higher than an average level of the sensed signal, and any sensed signal having associated value higher than the first threshold is associated with a surface pattern classified as a broken cavity defect. According to a second detection function, the sensed signal is further discriminated by a second threshold that is lower than the average level of the sensed signal, and any sensed signal having associated value lower that the first threshold is associated with a surface pattern classified as a crack or pinhole defect. A final discrimination between these two types of defects is obtained through analysis of the relation between the contour and the length or area of the defect pattern. However, while direct measurement of defect area in a plane passing through the object surface is carried out, the surface profile as measured in a direction perpendicular to the surface cannot be considered as a complete and accurate representation of the actual surface profile. Furthermore, the threshold values employed, which must be determined through experiments, cannot be considered as being directly proportional to or accurately representative of the desired dimensional limits for defects as set by an operator.

To obviate these limitations, systems employing optical ranging devices to provide surface profile measurements have been proposed. Such a system is disclosed in U.S. Pat. No. 5,083,867 issued on Jan. 28, 1992 to Burk, which system comprises a monochromatic light source such as laser for directing at an acute angle a beam of light forming a line upon a surface of an object to be inspected, and a camera for generating image signals that are representative of light reflected from the surface. In response to the image signals, a processor, through triangulation calculation, produces profile data corresponding to the contour of the illuminated surface profile, which data can be used by the processor to determine certain characteristics of the object, such as surface distortion or other defects.

Experience has shown that successful applications of known optical ranging system to surface defects detection using predetermined thresholds are generally limited to inspection of articles characterized by substantially stable surface orientation and position of the scanned area in relation to a reference system which is generally defined by the optical sensor. However, in a production lumber processing line, to maximize production rate, it is advantageous to freely guide and feed with a transport conveyor a lumber piece to be inspected into the inspection area in a free standing mode, without holding article in a firm predetermined position on the conveyer, which would be otherwise required with prior art surface defects detection techniques. Furthermore, prior art techniques generally cannot provide high resolution required for detecting geometrical surface defects such as wane, cavities or missing wood zones, which are not necessarily associated with characteristic shade or color. Dimensional measurements of such geometrical surface defects generally cannot be provided with brightness-based detection techniques.

SUMMARY OF THE INVENTION

It is thus a feature of the present invention to provide an apparatus and a method for detecting surface defects on articles presenting surface orientation variations.

According to the above feature, from a broad aspect, the present invention provides an apparatus for detecting surface defects on an article being conveyed in a scanning direction. The apparatus comprises surface shape inspection means for obtaining profile data of at least one surface of the article at a cross-section, said profile data being referenced to a reference system. The apparatus further comprises data processing means for deriving a base reference curve from generally regular portions of the profile data. Defect detecting means is provided for comparing the profile data with the base reference curve to recognize a defect induced departure of the profile data with respect to the base reference curve and to produce a defect output signal.

According to another aspect of the present invention, there is provided an apparatus for detecting missing wood on at least one surface of a wooden article having at least one pair of opposed surfaces, said article being conveyed in a scanning direction. The apparatus comprises surface shape inspection means for obtaining profile data of the pair of opposed surfaces at a cross-section, the profile data being referenced to a reference system. The apparatus further comprises data processing means for deriving at least a pair of base reference curves from generally regular portions of the profile data. A missing wood detecting means is provided for measuring spacing between the pair of base reference curves to recognize a defect induced spacing departure from a predetermined minimum spacing to produce a defect output signal.

According to a further aspect of the invention, there is provided an apparatus for detecting longitudinal surface defects on an article being conveyed in a scanning direction. The apparatus comprises surface shape inspection means for obtaining profile data of at least one surface of the article at successive cross-sections, the profile data being referenced to a reference system. The apparatus further comprises data processing means for deriving a plurality of successive base reference curves from generally regular portions of the profile data. There is provided defect detecting means comparing adjacent ones of the base reference curves to recognize position shift data for corresponding adjacent ones of the cross-sections and to produce a defect output signal indicative of a surface defect extending along the surface whenever values of the position shift data is higher than a predetermined defect threshold value.

According to a still further aspect of the present invention, there is provided an apparatus for detecting surface defects on an article. The apparatus comprises surface shape inspection means for obtaining profile data of at least one surface at successive cross-sections, said profile data being referenced to a reference system, the surface shape inspection means being displaceable with respect to said at least one surface in a scanning direction. The apparatus further comprises data processing means for deriving successive base reference curves from generally regular portions of the profile data. There is provided defect detecting means comparing the profile data with the successive base reference curves to recognize a defect induced departure of the profile data with respect to the base reference curves and to produce a defect output signal.

According to a further broad aspect of the present invention, there is provided a method for detecting surface defects on an article, the method comprising steps of: i) obtaining profile data of at least one surface of the article at a cross-section, said profile data being reference to a reference system; ii) deriving a base reference curve from generally regular portions of the profile data; (iii) comparing the profile data with the base reference curve to recognize a defect induced departure of the profile data with respect to the base reference curve; and iv) producing a defect output signal.

According to a still further aspect of the present invention, there is provided a method for detecting missing wood on at least one surface of a wooden article having at least one pair of opposed surfaces. The method comprises steps of: i) generating profile data of the pair of opposed surfaces at a cross-section, said profile data being referenced to a reference system; ii) deriving at least a pair of base reference curves from generally regular portions of the profile data; iii) measuring spacing between the pair of base reference curves to recognize a defect induced spacing departure from a predetermined minimum spacing; and iv) producing a defect output signal.

According to a still further aspect of the present invention, there is provided a method for detecting longitudinal surface defects on an article. The method comprises steps of: i) generating profile data of at least one surface of the article at successive cross-sections, the profile data being referenced to a reference system; ii) deriving a plurality of successive base reference curves from generally regular portions of the profile data; iii) comparing adjacent ones of the base reference curves to recognize position shifts for corresponding adjacent ones of the cross-sections; iv) producing a defect output signal indicative of a surface defect extending along the surface whenever values of the position shifts are higher than a predetermined defect threshold value.

BRIEF DESCRIPTION OF THE DRAWINGS

Preferred embodiments of the present invention will now be described with reference to the accompanying drawings in which.

DETAILED DESCRIPTION OF THE PREFERRED EMBODIMENTS

Figure 1:
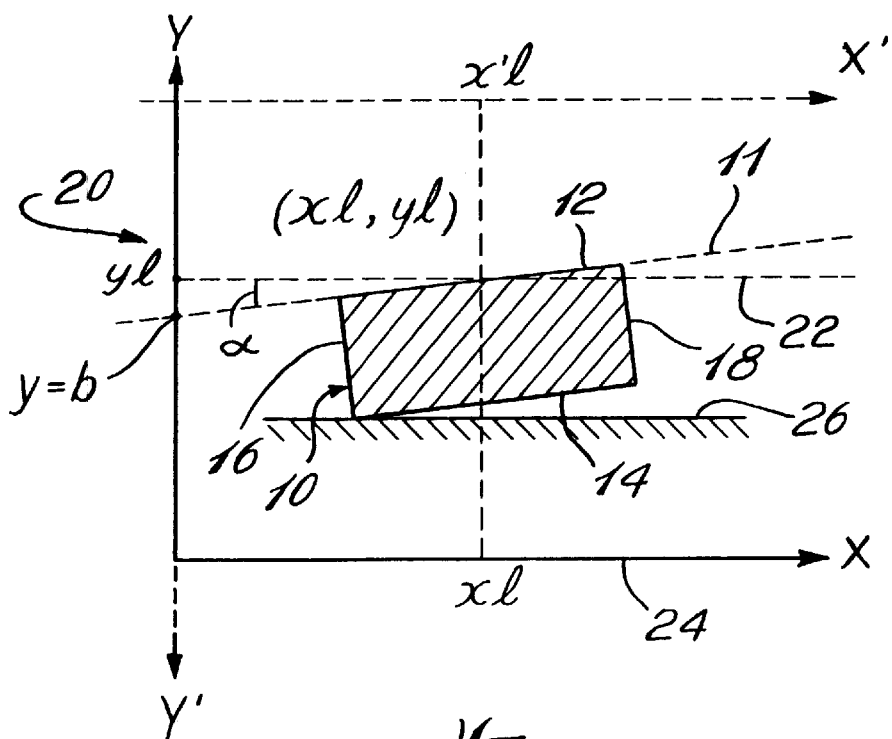
FIG. 1 is a graph showing a cross-sectional view of an article to be inspected laying on a conveyor and a reference curve in relation with a reference system according to the present invention.

Referring now to FIG. 1, an article 10 to be inspected is shown in a free-standing position and has opposed upper and lower surfaces forming profile traces 12 and 14 and opposed side surfaces forming profile traces 16 and 18, which profile traces form a complete profile of the article 10 at a given cross-section. It can be seen that for an elongated article having a generally uniform rectangular section as shown in FIG. 1, the profile traces 12, 14, 16 and 18 cross a cross-section plane defined by a system X-Y as designated at numeral 20, thereby defining a set of profile curves that can be generally represented by reference curves defined by straight line equations. It is to be understood that articles showing other cross-section shape can be inspected according to the present invention, provided reference curves can be defined either mathematically or empirically. In the example shown if FIG. 1, to the upper profile trace 12 corresponds a reference curve 11, which is a straight line in the example shown, that can be mathematically represented as follows:

$$y = ax + b \quad (1)$$

with $$a = \frac{\Delta y}{\Delta x} \quad (2)$$

wherein a is the slope of the line and b is the value of y at x=0.

Figure 2:
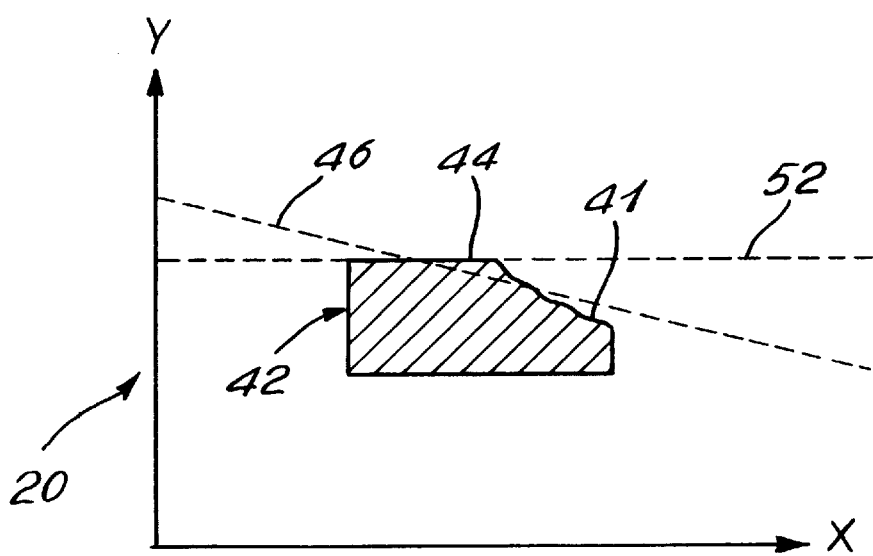
FIG. 2 is a graph showing a cross-sectional view of an article to be inspected having a defective surface profile with a corresponding reference curve in relation with the reference system.
Figure 3:
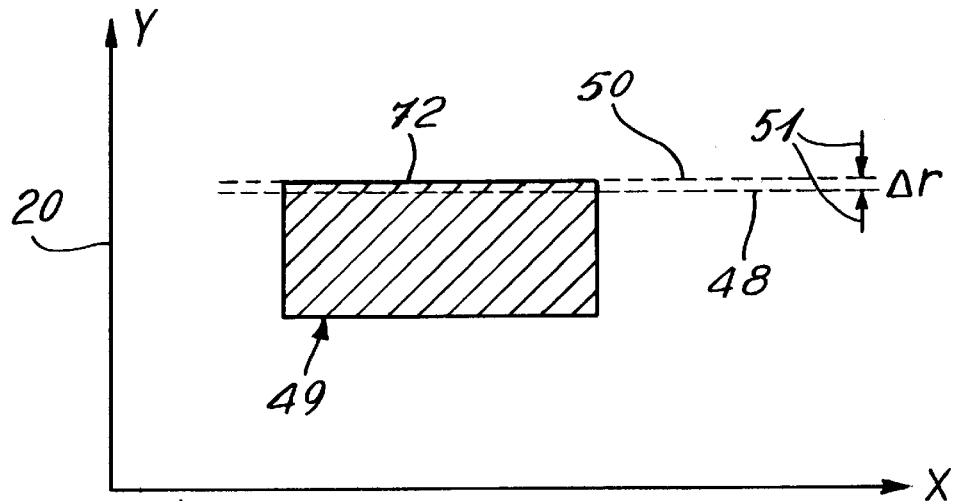
FIG. 3 is a graph showing a transverse cross-sectional view of an article to be inspected article and curve fitting threshold curve in relation to the reference system.

It is pointed out that for an elongated article as shown in FIG. 1, the reference curve 11 of profile trace 12 forms at its specific position along the length of the article, a non-null angle α with reference to a projection 22 of the X axis 24, which means that only a portion of the lower surface 14 bears on a conveyer 26, since the article is twisted about its longitudinal axis as it is often the case with wooden articles such as lumber pieces. While the angle α represents orientation of the reference curve 11 and corresponding surface 12, position thereof can be represented by a single point having coordinates $(x_1, y_1)$ in the system X-Y of FIG. 1. It is pointed out that other proper system, such as X'-Y' as shown in FIG. 1, can be chosen for representing the position of any of the reference curves corresponding to profile traces 12, 14, 16 and 18. As will be later explained in more detail, according to the present invention, any of profile 12, 14, 16 and 18 can be scanned to generate corresponding profile trace data characterizing the surface topology, which data consisting of a series of points coordinates measurements along the profile line. As can be seen with reference to FIG. 4, a plurality of successive profile traces 32, 34 and 36 are spaced in a parallel relationship along a surface 38 of a lumber piece 30 under inspection. For reliable surface defects detecting purposes, it is essential to identify points on the article surface under inspection which belong to flawless portions of the surface, as opposed to defective portions such as those presenting cavity 38 and wane 41, the flawless portions being substantially characterized by surface portions regularity. As can be seen with reference to the article 10 as shown in FIG. 1, points of a surface that belong to a corresponding reference curve can be easily identified. However, for an article presenting a defective surface portion such as a lumber piece 42 having wane portion 41 as shown in FIG. 2, determination of the reference curve for the straight surface portion 44 requires a particular derivation method. According to a preferred embodiment of the present invention, a data processing device, which will later described in more detail with reference to FIG. 10, performs conventional mathematical curve fitting algorithm, such as linear regression method, using points coordinates of the profile data as scanned. If one considers all points of the surface profile, a regression calculation would yield to a wrong reference curve 46, due to points of the defective portion 41. As shown in FIG. 3, in order to obviate this problem, the linear regression calculation considers only surface points of the article 49 which have coordinates positioned over a predetermined linear regression threshold curve 48 presenting a shift Δr, as indicated by arrows 51, under an initial reference curve 50 corresponding to profile trace of a surface 72. Through linear regression over selected points of the profile data, a resulting base reference curve 52 can be derived, as shown in FIG. 2, which base reference curve 52 has proper position and orientation in relation to the X-Y reference system 20.

Figure 4:
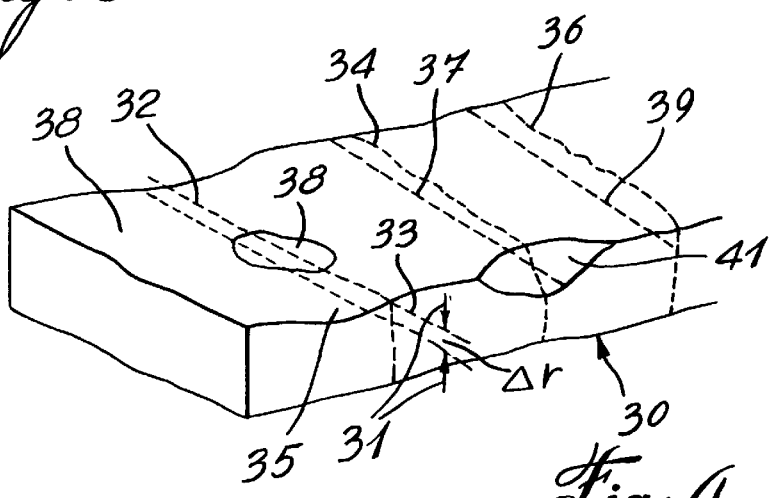
FIG. 4 is a partial perspective view of a lumber piece to be inspected according to the present invention, showing successive profile traces on the surface thereof.

According to a preferred embodiment, the data processing device stores characteristic information about the base reference curve upstream from the cross-section under scanning to predict the base reference curve without relying exclusively on the profile data for the cross-section under scanning. In the example as shown in FIG. 3, data associated with initial reference curve 50 can define an arbitrary horizontal straight line starting at a surface point having highest coordinates for a first base reference curve data derivation and thereafter cause to define a prior base reference curve obtained through prior curve fitting derivation from the profile data. With reference to FIG. 4, this process can be defined as the followings steps: a) defining an initial reference curve 33 corresponding to the scanned cross-section defining profile trace 32, b) defining a threshold curve 35 shifted with respect to the first reference curve 33 by a predetermined threshold value Δr, as indicated by arrows 31 c) selecting elements of the profile data which have values being higher than the threshold curve 35, d) applying a curve fitting calculation to derive the base reference curve, which has not been represented in FIG. 4 for purposes of clarity, and e) repeating the steps a) to d) to derive following base reference curves corresponding to a following cross-section defining profile traces 34 and 36, respectively using threshold curves 37 and 39.

Figure 5:
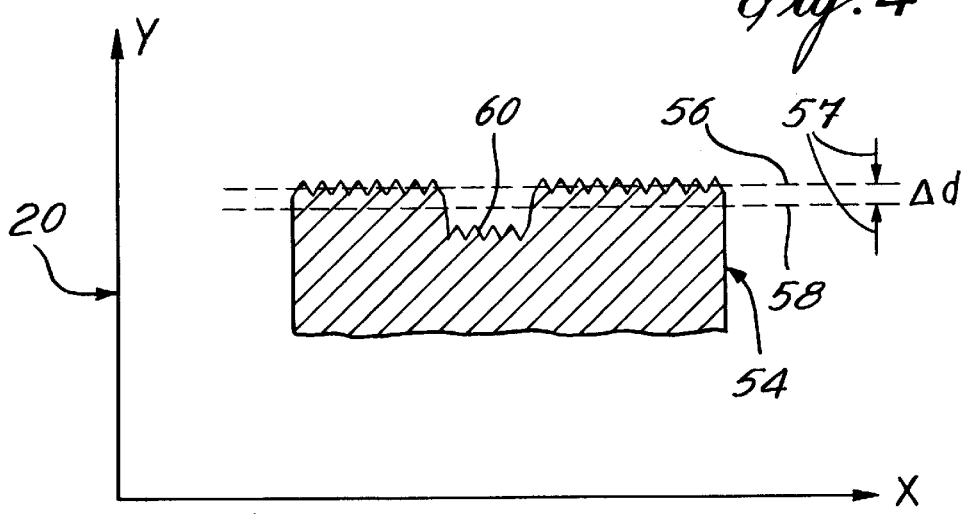
FIG. 5 is a graph showing a cross-sectional view of a lumber piece to be inspected having roughness and cavity defects and showing reference and defect threshold curves in relation with the reference system.

Turning now to FIG. 5, there is illustrated a lumber piece 54 to be inspected having roughness and cavity defects. A base reference curve 56 as obtained through curve fitting is shown with a defect threshold curve 58, in relation with the reference system 20. The defect threshold curve 58 is associated with a particular defect to be detected, and is shifted inwardly with respect to the base reference curve 56 and corresponding data, by a predetermined threshold value Δd, as indicated by arrows 57. As will be later described in more detail, the apparatus according to the present invention comprises a defect detecting device comparing the profile data the corresponding base reference curve to recognize a defect induced departure of the profile data with respect to the base reference curve and to produce a defect output signal. More specifically, the defect detecting device compares said profile data with said base reference curve using a defect threshold curve being shifted inwardly with respect to the base reference curve by a predetermined threshold value Δd, to select elements of the profile data which satisfy a first specific condition. The defect output signal being associated with the selected elements of the profile data, it can be further indicative of position of the detected defect along the profile trace. For detection of surface defects that are characterized by roughness of a portion of the surface under inspection, as a first specific condition, Δd is chosen so as to select all points which have coordinates substantially positioned outwardly over the defect threshold line through comparison of the profile data with the corresponding defect threshold line, thereby excluding surface points associated with deeper defects such as the cavity 60. According to a preferred embodiment of the present invention, for a given cross-section, the defect output signal is produced whenever:

$$\frac{\sum_{i=1}^{n} |x_i - x_{i+1}|}{n} \geq R \quad (3)$$

wherein:

$x_i$ represents departure value of a selected data element i among selected data elements of the profile data from the base reference curve, with i=1,n;

n is a total number of selected elements; and

R is a predetermined roughness threshold value.

In a case where successive cross-sections are being scanned, the defect output signal is produced whenever:

$$\frac{\sum_{i=1}^{n_j} |x_i - x_{i+1}|}{n_j} \geq R$$

wherein $x_{i,j}$ represents departure value of a selected data element i among selected data elements of the profile data from the base reference curve for a cross-section j of said successive cross-sections, with i=1,n, and j=1,m;

$n_j$ is a total number of said selected elements for said cross-section j;

m is the number of said successive cross-section; and

R is a predetermined roughness threshold value.

So as to provide cavity detection, an associated defect threshold line can be used based on a proper value of Δd. In the particular example as shown in FIG. 5, a single defect threshold curve used for both roughness and cavity detection is proposed. For the detection of the cavity 60, the apparatus selects all points having coordinates substantially positioned under the defect threshold curve 58 through comparison of the profile trace data with the corresponding defect threshold curve 58. So as to avoid associating a normal surface crack with a cavity defect, a specific condition may require that a total number of the selected elements is higher that a predetermined cavity threshold value for the profile trace. It is to be understood that further data processing can be provided, such as derivation of number of cavities along a profile trace or along a completely scanned article.

Figure 6:
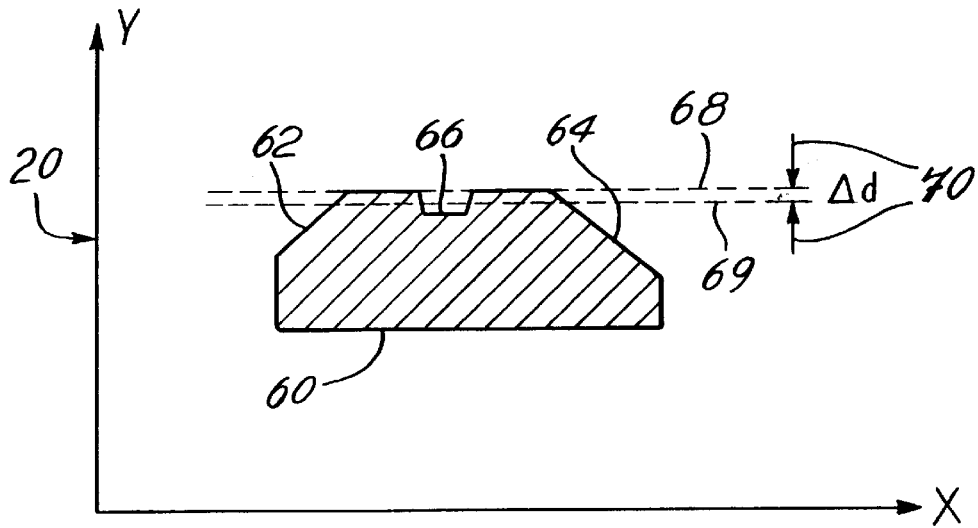
FIG. 6 is a graph showing a transverse cross-sectional view of a lumber piece to be inspected characterized by wane portions and showing reference and defect threshold curves in relation with the reference system.

The present invention is further useful for detecting geometrical surface defects found in lumber, such as wane or missing wood. Referring to FIG. 6, a lumber piece 60 presents wane portions 62 and 64 at external edges of the profile traces. A cavity 66 is also present at an upper surface of the lumber piece 60. To properly detect wane at both edge portions of the lumber piece 60, base reference curves 68 and defect threshold curve 69 are derived according to the method explained before, using a predetermined threshold value 66 d as indicated by arrows 70. In this case, the specific condition that has with be satisfied in order to detect wane requires that the elements of the profile trace data corresponding to one or more of the successive cross-sections, have coordinates in relation to the reference system being substantially under the corresponding defect threshold curve 69 and associated to external end portions or edges 62 and 64 of the profile trace. Furthermore, to avoid associating acceptable edge irregularities with wane, the specific condition further requires that a total number of the selected elements is higher that a predetermined wane threshold value for the profile trace.

Figure 7:
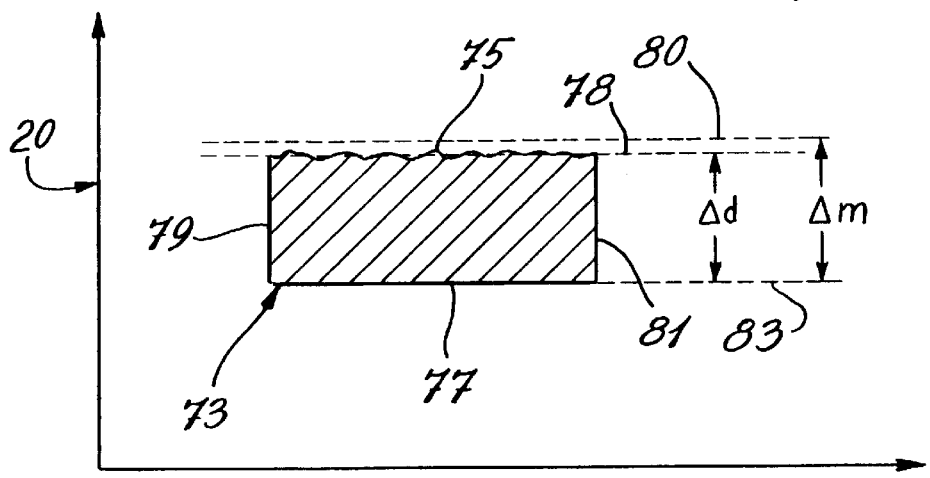
FIG. 7 is a graph showing a transverse cross-sectional view of a lumber piece to be inspected characterized by missing wood and showing a pair of reference curves in relation with the reference system.

Turning now to FIG. 7, missing wood detection will now be explained. The wooden article 73 has a first pair of opposed surfaces 75 and 77, and a second pair of opposed surfaces 79 and 81, which surfaces define a complete profile cross-section in relation with the system 20, as earlier explained. For the purposes of detecting missing wood on the surface 75, data defining opposed reference curves 78 and 83 corresponding to one or more of opposed successive profile traces associated with the pair of opposed surfaces 75 and 77 is process to derive spacing Δd between the pair of base reference curves 78 and 83 to recognize a defect induced spacing departure from a predetermined minimum spacing Δm and to produce a corresponding defect output signal.

Figure 8:
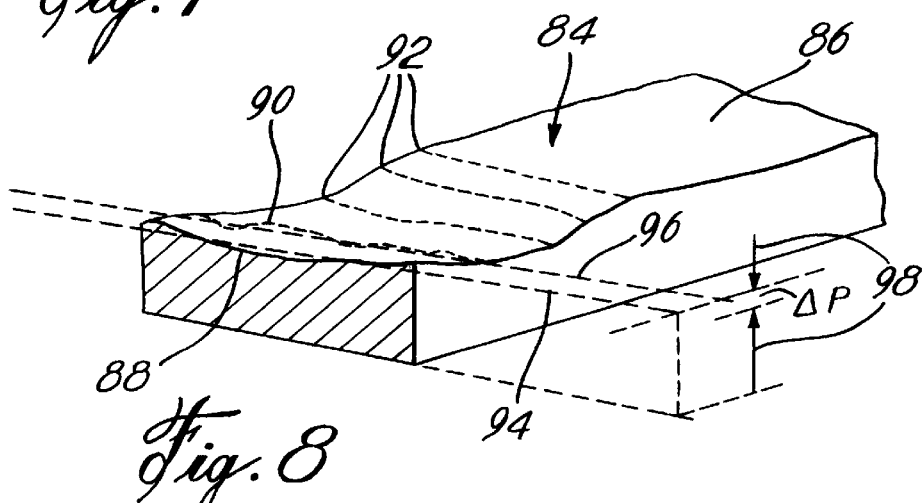
FIG. 8 is a partial perspective view of an article to be inspected which shows a surface defect extending longitudinally on the article surface in relation to reference curves.

Turning now to FIG. 8, detection of longitudinal defects on a wooden article according to the present invention will be described. An article 84 to be inspected having an upper surface 86 is scanned by the surface shape inspection device to produce profile trace data corresponding to a plurality of successive cross-sections defining profile traces 88, 90 and 92 spaced in a parallel relationship along the inspected surface 86. Successive base reference curves data from said trace data are derived by the data processing device according to the method explained before. The defect detecting device then compared adjacent reference curves 94 and 96 to recognize position shift data Δp as indicated by arrows 98, for corresponding adjacent cross-sections, and to produce a defect output signal indicative of a surface defect extending along the inspected surface 86 whenever values of the position shift data Δp is higher than a predetermined defect threshold value.

Figure 9:
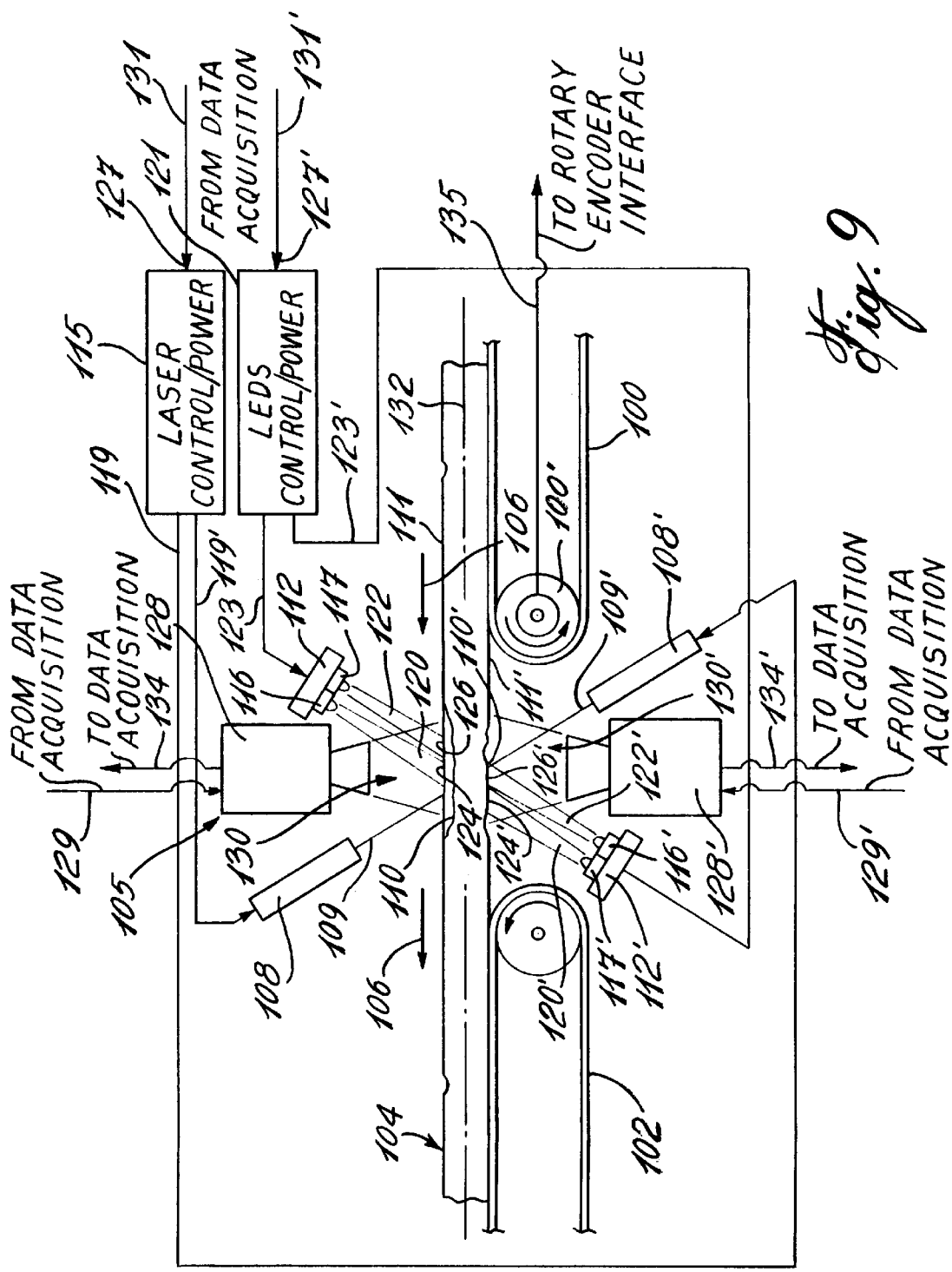
FIG. 9 is a partial side view of a first preferred embodiment of an apparatus according to the present invention illustrating the shape inspection unit including a single pair of cameras an showing an article transported by a conveyor system in a longitudinal scanning direction and being illuminated by the laser and color light sources.

Referring now to FIG. 9, a first preferred embodiment of an apparatus according to the present invention will be explained. The apparatus comprises a transport system including a feeding belt conveyor 100 in series with an output conveyor 102, which conveyors are driven by an electric motor (not shown). An article 104 to be inspected, which is a lumber piece in the example shown, is being displaced upon conveyers 100 and 102 driven in a forward direction as indicated by arrows 106. The surface shape inspection unit provided one the apparatus comprises a conventional optical ranging unit 105 including monochromatic light emitting sources such laser sources 108 and 108' respectively projecting laser beams 109 and 109' onto opposed article surfaces 111 and 111' forming profile traces 110 and 110' respectively thereon. It can be seen on FIG. 9 that driving of the conveyers 100 and 102 create a relative movement between the article 104 and the optical ranging unit 105 for article scanning purposes. It has been found that for certain types of defects, such as altered wood on lumber surface, color analysis is required combined with cavity or roughness defect detection, as will be later explained in more detail. For this purpose, a pair of light source units 112 and 112' are provided with first and second light emitting diodes (LED) linear arrays 116, 117 and 116', 117', which arrays of LEDs are characterized by two different wavelengths, as will be later explained in more detail. The LEDs arrays 116 and 117 respectively project onto the article top surface 111 light beams 120 and 122 that cover separate transverse areas 124 and 126 of the surface 111. In a same way, the LEDs arrays 116' and 117' respectively project onto the underneath article surface 111' light beams 120' and 122' that cover separate transverse areas 124' and 126' of the surface 111'. Since projected beams of LEDs arrays 116, 117 and 116', 117' intersect distinct areas on the article 104, they may be simultaneously powered. However, alternating switching is preferred to avoid light interference, enabling some areas overlap without causing undesirable effect. Respective spacing between LEDs arrays 116, 117 and the laser 108 is set so that distances between the profile line 110 and the illuminated areas 124 and 126 are multiple factor values of the displacement of the article in the direction of the arrow 106 which occurs during the time separation between two successive image frames as captured by the camera 128. A rotary encoder 125 is mounted on a roll 100' of the conveyer 100 to generate pulses signals sent to the data processing unit through line 135 and rotary encoder interface for time synchronization purposes, as will be later explained in more detail. Respective spacing between LEDs arrays 116', 117' and profile lasers 108' is set accordingly. In this way, points of the surface 111 corresponding to a given image frame of the profile traces 110 also correspond to other image frames for illuminated transverse areas 124 and 126, whereby profile and color data for a same surface point or area can be derived. It is to be understood that other types of illumination sources can be used, such as conventional polychromatic light sources with proper color filters altering the light beams either before or after reflection on the article surface. Furthermore, conventional polychromatic light sources can be used directly without any color filter by providing a color spectrum analyzing device receiving color image signal from a color camera. Returning to FIG. 9, a pair of opposed pixel matrix cameras 128 and 128' of CCD type or the like are respectively disposed over and under space provided between the conveyers 100 and 102. To meet high conveyers speed, two fast-framing cameras having 128×128 pixels were used, each producing 840 frame/sec of reflectance signals. The cameras 128 and 128' are substantially vertically equally spaced from a central horizontal plane 132 passing through the article 104 in a substantially parallel spaced relationship with opposed surfaces 111 and 111'. The camera 128 is positioned in a such manner that its field of vision 130 intersects the top surface 111 to scan the illuminated areas 124, 126 and the profile trace 110. In a same way, the camera 128' is positioned in a such manner that its field of vision 130' intersects the underneath surface 111' to scan the illuminated areas 124', 126' and the profile trace 110'. Alternately, in addition to the cameras 128 and 128', independent color sensing devices such as two additional cameras respectively associated with illuminated areas 124, 126 and 124', 126' can be provided. A laser control/ power unit 115 is connected through power lines 119 and 119' respectively to the laser 108 and 108' for energizing thereof. For a same purpose, a LEDs control/power unit 121 is connected through power lines 123 and 123' respectively to the LED's arrays 116, 117 and 116', 117'. The laser and LEDs control/ power units 115 and 121 receive, through respective inputs 127 and 127' provided thereon and lines 131 and 131', control signals from a data acquisition unit, as will be later explained. While the cameras 128 and 128' send image signals to data acquisition units through lines 134 and 134', as will be explained later in more detail. Framing synchronization signals for the cameras 128 and 128' are sent by the data acquisition units through lines 129 and 129', as will be later discussed in more detail.

Figure 10:
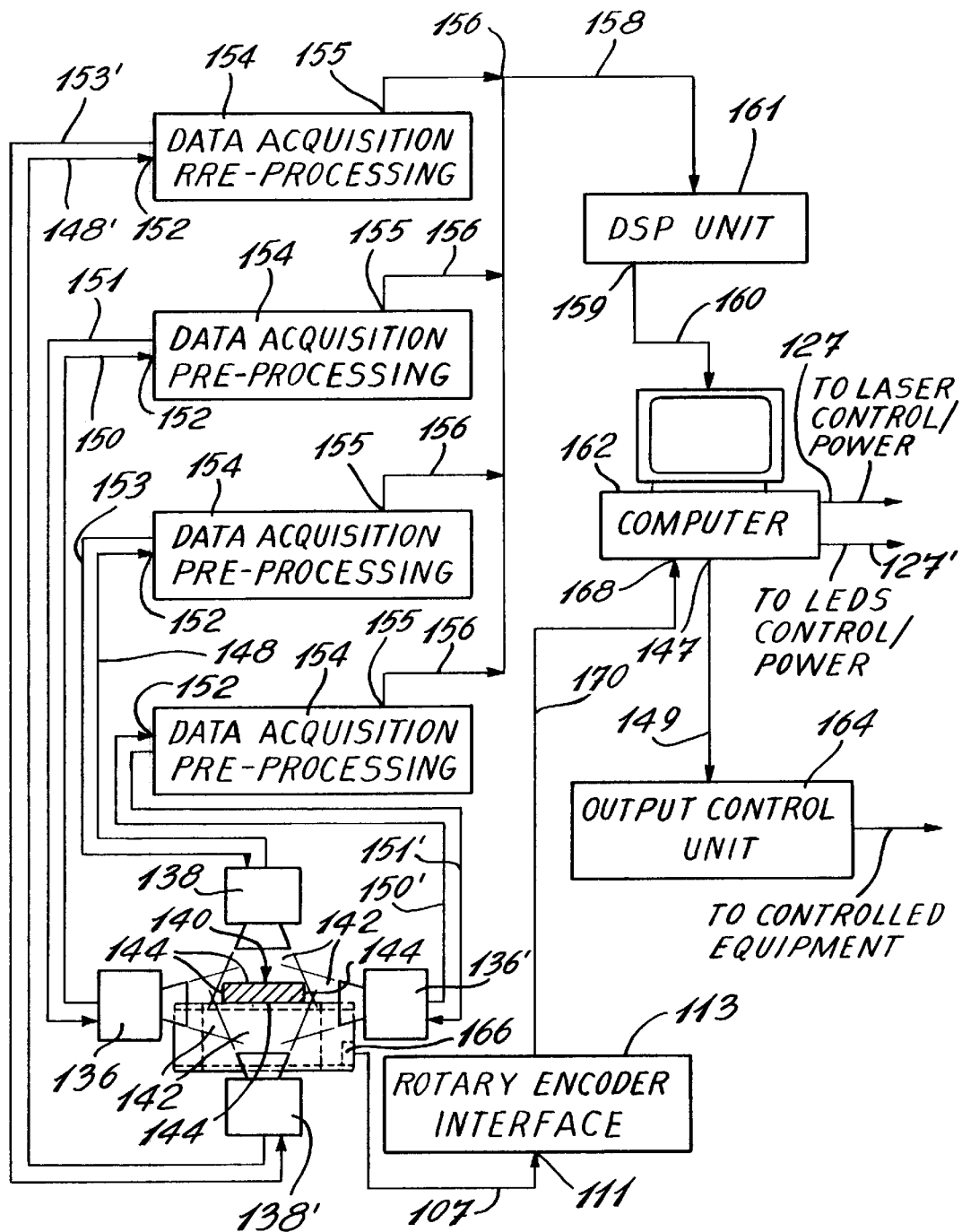
FIG. 10 is a block diagram of the apparatus according to a first preferred embodiment of the present invention, showing the optical system including two pairs of cameras.

Referring now to FIG. 10, there is illustrated a block diagram of the present apparatus showing an optical system including two pairs of opposed cameras 136, 136' and 138, 138' having respective field of view 142 intersecting a corresponding surface 144 of an article 140 under inspection. Image signals corresponding to all image pixels from the cameras 136, 136', 138 and 138' are sent via lines 148, 148', 150 and 150' to a respective input provided on data acquisition and pre-processing units 154 arranged in parallel configuration. Outputs 156 provided on units 154 communicates through lines 156 and main bus 158 to a data processing device such as a Digital Signal Processor (DSP) unit 161 having a digital output 159 linked to a computer 162 through a line 160. The DSP unit may comprise four DSP processors operating in a parallel manner to increase processing speed. The data acquisition and pre-processing units 154 performs selection of pixels related to profile traces and illuminated areas only, thereby excluding non-significant pixels to enhance further speed processing. The units 154 also provide electrical coupling between the cameras and the DSPs, and transmission of the selected pixel signals to the DSPs through a standard bus such as DSP-LINK. As mentioned before, the units 154 provide framing synchronization for cameras 136, 136', 138 and 138' through lines 151, 151', 153 and 153', and are further connected to output lines 127 and 127' for sending control signals to the laser control/power and LEDs control/power units respectively. The computer 162 provides switching synchronization control of the LEDs arrays of different wavelengths, and switching control of the lasers according to a predetermined pulse duration. Furthermore, the units 154 may be provided with a buffer memory to store values of the selected digital signals for all the surfaces of the article 140 for further processing. The DSP unit 161 performs all calculation and defects detection from selected pixel signals relating to a given image frame. In turn, the computer 162 performs classification of detected defects considering all frames and scanned surfaces 144 of the article 140. To associate each image frame with a corresponding cross-section position along the article 140, coupled to any of the driven or driving rolls of the conveyers 100 and 102 is a rotary encoder 166 detecting roll rotation to send through a line 107 a series of pulse signals to an input 111 provided on an interface unit 113, which comprises pulse counter device for sending through an output 169 provided thereon and a line 170 a computed pulses signal to a computer input 168. Furthermore, from displacement data, the computer 162 can derive article speed using its internal clock. The computer 162 sends through output 147 and line 149 control signals to an output control unit 164 that may drive equipment such as marking unit, sorting device or sawing apparatus.

Figure 11:
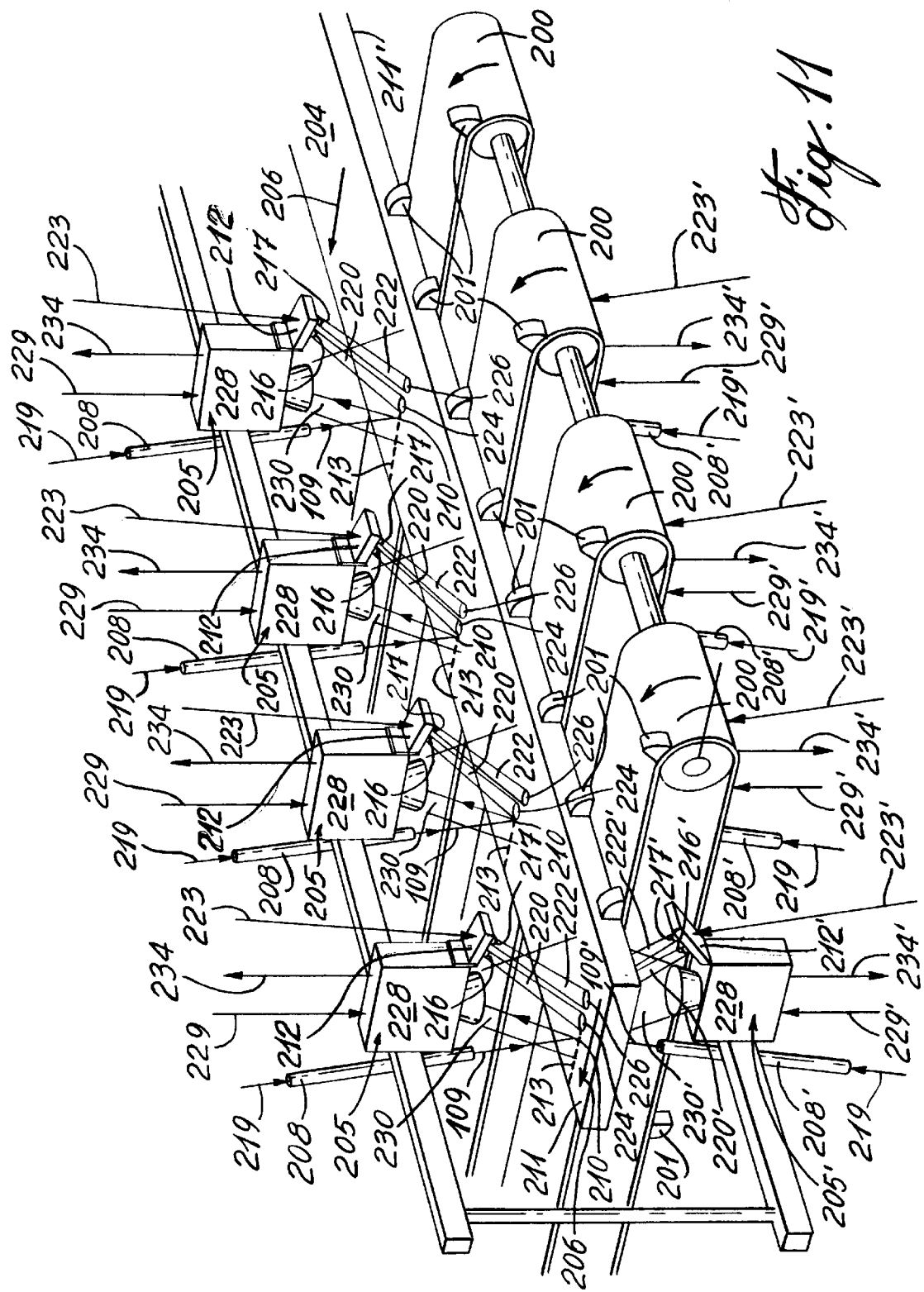
FIG. 11 is a partial perspective view of a second preferred embodiment of an apparatus according to the present invention illustrating the surface shape/color measurement unit including a series of pair of cameras and light sources and showing an article transported by a conveyor system in a transverse scanning direction.

Referring now to FIG. 11, a second preferred embodiment of an apparatus according to the present invention will be described. The apparatus comprises a transport system including a plurality of parallel spaced belt conveyors 200 in series with feeding conveyors (not shown), which conveyers are driven by an electric motor (not shown). The Belt conveyors 200 are provided with a plurality of protruding abutments 201 providing proper alignment of the article 204 to be inspected. An article 204 to be inspected, which is a lumber piece in the example shown, is being displaced by belt conveyors 200 being driven in a transverse forward direction with respect to the lumber piece 204 as indicated by arrows 206. The apparatus comprises a surface shape inspection device comprising two rows of parallel spaced optical ranging unit 205 and 205' including monochromatic light emitting sources such laser sources 208 and 208' respectively projecting laser beams 109 and 109' onto opposed article surfaces 211 and 211' forming spots 210 thereon. It can be seen on FIG. 11 that driving of the conveyers 200 create a relative movement between the article 204 and optical ranging units 205 and 205' whereby the spots 210 follow respective traces 213 onto article surfaces for lengthwise scanning purposes. For color detection purposes as explained before, light source units 212 and 212' are respectively mounted on each optical ranging unit 205 and 205', which light source units are respectively provided with first and second light emitting diodes (LED) 216, 217 and 216', 217', which LEDs are characterized by two different wavelengths, as will be later explained in more detail. The LEDs 216 and 217 respectively project onto the article top surface 211 light beams 220 and 222 which are aligned with laser beam 109. In a same way, the LEDs 216' and 217' respectively project onto the underneath article surface 211' light beams 220' and 222' aligned with laser beam 109'. Since projected beams of LEDs 216, 217 and 216', 217' intersect distinct areas on the article 204, they may be simultaneously powered. However, as mentioned before, alternating switching is preferred to avoid light interference, enabling some areas overlap without causing undesirable effect. Respective spacing between LEDs 116, 117 and respective laser 208 is set so that distance between the spots 210 and the illuminated areas 224 and 226 are multiple factor values of displacement of the article in the direction of the arrow 206 which occurs during the time separation between two successive image frames as captured by the linear cameras 228 and 228' provided in each optical ranging unit 205 and 205'. In a same manner, respective spacing between LEDs 116', 117' and lasers 208' is set accordingly. In this way, points of the surface 211 or 211' corresponding to a given image frame of the spots 210 also correspond to other image frames for illuminated areas 224 and 226 or 224' and 226', whereby profile trace and color data for a same surface point or area can be derived. The cameras 228 and 228' are substantially vertically equally spaced from a central horizontal plane passing through the article 204 in a substantially parallel spaced relationship with opposed surfaces 211 and 211'. Each camera 228 is positioned in a such manner that its field of vision 230 intersects the top surface 211 to scan the illuminated areas 224 and 226, profile trace 213 and spot 210. In a same way, each camera 228' is positioned in a such manner that its field of vision 230' intersects the underneath surface 211' to scan corresponding illuminated areas, profile trace and spot. A laser control/power unit (not shown) is connected through power lines 219 and 219' respectively to the laser 208 and 208' for energizing thereof. For a same purpose, a LEDs control/power unit (not show) is connected through power lines 223 and 223' respectively to the LED's 216, 217 and 216', 217'. The laser and LEDs control/power units receive control signals from a data acquisition unit, in a same way as explained before. The cameras 228 and 228' send image signals to the data acquisition units through lines 237 and 237', as will be explained later in more detail. Framing synchronization signals for the cameras 228 and 228' are sent by the data acquisition units through lines 229 and 229'.

Figure 12:
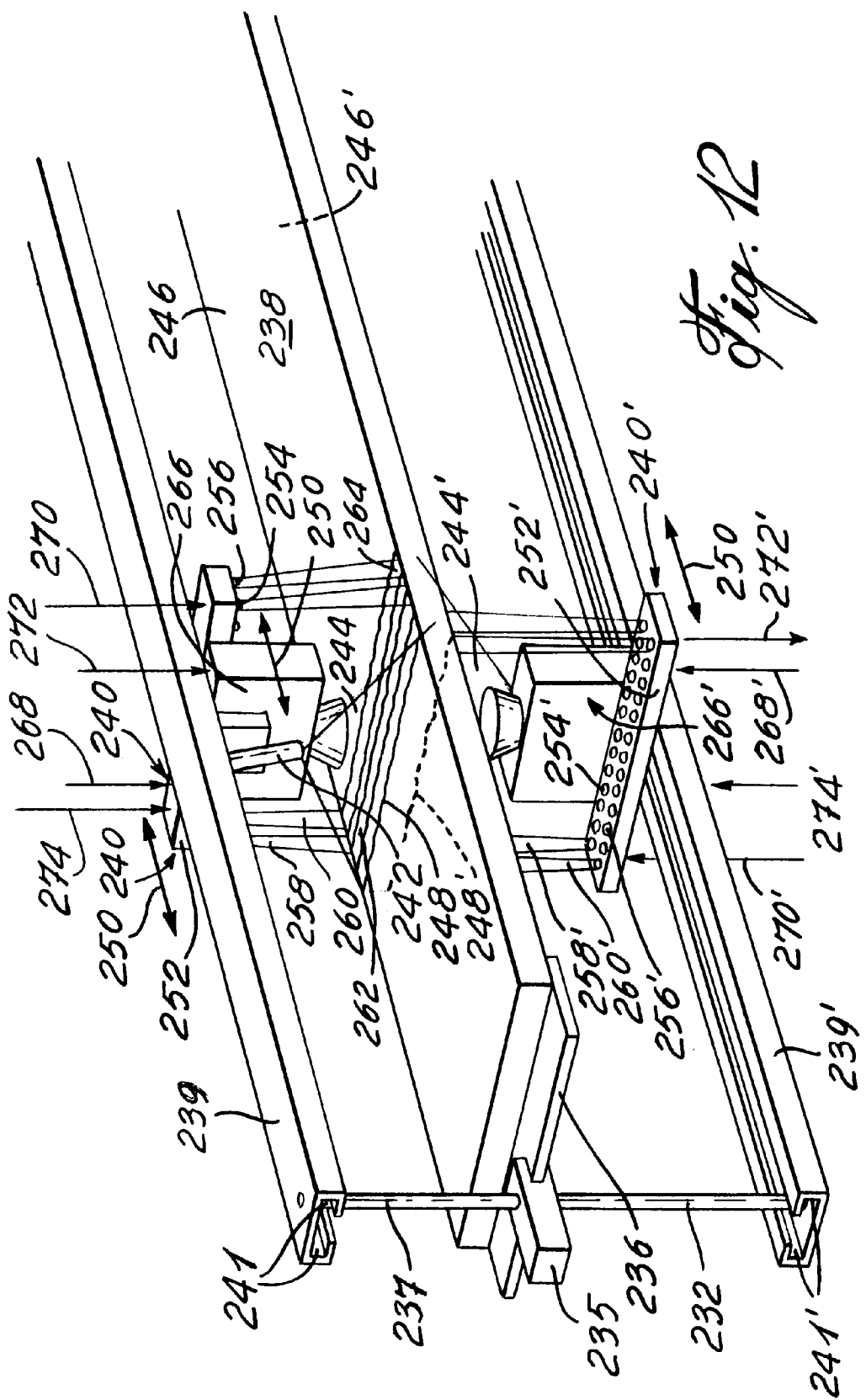
FIG. 12 is a partial perspective view of a third preferred embodiment of an apparatus according to the present invention illustrating a displaceable surface shape/color measurement unit movable along a longitudinal scanning direction with respect to a fixed article to be inspected.

Turning now to FIG. 12, a third embodiment of the apparatus according to the present invention will be described. The apparatus comprises a frame 232 comprising a pair of support posts 234 standing at the opposed end to the apparatus, only one of posts 234 being illustrated in FIG. 12. Secured to the posts 234 through attachments 235, is a pair of opposed support plates 236 bearing respective ends of an article 239' to be inspected, only one of attachments 235 and plates 236 being illustrated in FIG. 12. Also secured to the posts 234 is a pair of parallel spaced guide rails 238 and 238' on which are mounted displaceable surface shape inspection devices 240 and 240' through respective chain driven roller mounted carrier (not shown) housed in elongated grooves 241 and 241' extending within the guide rails 238 and 238', to provide controlled displacement of the inspection devices 240 and 240 along rails 238 and 238' through operation of a driving electric motor (not shown) connected to a controller provided in the apparatus. The displaceable surface shape inspection devices 240 and 240' respectively comprise optical ranging units including monochromatic light emitting sources such laser source 242 projecting laser beams 244 and 244' onto opposed article surfaces 246 and 246' to respectively form profile traces 248 and 248' thereon. It can be seen from FIG. 12 that displacement of the surface inspection devices 240 and 240' in a forward or rearward direction as indicated by arrows 250 create a relative movement between the article 238 and optical ranging units 240 and 240' for lengthwise scanning purposes. For color detection purposes as explained before, light source units 252 and 252' are provided on surface inspection devices 240 and 240', which light source units are respectively provided with first and second light emitting diodes (LED) arrays 254, 256 and 254', 256', which LEDs are characterized by two different wavelengths, as will be later explained in more detail. The LEDs arrays 254 and 256 respectively project onto the article top surface 246 transverse light beams 258 and 260. In a same way, the LEDs arrays 254' and 256' respectively project onto the underneath article surface 246' transverse light beams 258' and 260'. Here again, respective spacing between LEDs arrays 254, 256 and respective laser 242 is set so that distance between the profile trace 248 or 248' and the illuminated areas 262 and 264 are multiple factor values of displacement of the article 238 in the direction of the arrow 250 which occurs during the time separation between two successive image frames as captured by the linear cameras 266 and 266' provided in each surface inspection device 240 and 240'. In a same manner, respective spacing between LEDs arrays 254', 256' and associated laser (not shown) is set accordingly. In this way, points of the surface 246 or 246' corresponding to a given image frame of the profile trace 248 or 248' also correspond to other image frames for illuminated areas 262 and 264 or 262' and 264', whereby profile trace and color data for a same surface point or area can be derived. The cameras 266 and 266' are substantially vertically equally spaced from a central horizontal plane passing through the article 238 in a substantially parallel spaced relationship with opposed surfaces 246 and 246'. The camera 266 is positioned in a such manner that its field of vision intersects the top surface 246 to scan the illuminated areas 262, 264 and the profile line 248. In a same way, the camera 266' is positioned in a such manner that its field of vision intersects the underneath surface 246' to scan the illuminated areas (not shown) and the profile line 248'. A laser control/power unit (not shown) is connected through power lines 268 and 268' to the respective laser 208 for energizing thereof. For a same purpose, a LEDs control/power unit (not shown) is connected through power lines 270 and 270' respectively to the LEDs arrays 254, 256 and 254', 256'. The laser and LEDs control/power units receive control signals from a data acquisition unit, in a same way as explained before. The cameras 266 and 266' send image signals to the data acquisition units through lines 272 and 272', as will be explained later in more detail. Framing synchronization signals for the cameras 266 and 266' are sent by the data acquisition units through lines 274 and 274'.

Operation of the apparatus according to the present invention will be now explained in more detail. Referring again to FIG. 9, the article 104 to be inspected is continuously displaced by the conveyors 100 and 102 in the direction of the arrow 104 and pass through the space provided between the conveyors 100 and 102. As soon a leading front edge of the surface 111 begins to reflect the light beam generated by the LEDs array 117, the camera 128 sends a corresponding image signal to the associated data acquisition and pre-processing unit 154, which compare pixel intensities with a predetermined first threshold value for starting processing. Similarly, end of processing occurs whenever the LEDs array 116 detects a trailing edge of the surface 111 corresponding to a second threshold value. The lasers 108 and 108' are energized through the laser control/power unit 115 according to control signals coming from the computer 164, as shown in FIG. 10. The lasers 108 and 108' are being operated in a pulse mode synchronized with the cameras 128 and 128' to limit exposure time at a minimum level providing proper image intensity according to the camera sensibility, thereby avoiding undesirable image averaging. The profile traces 110 and 110' are respectively sensed by the cameras 128 and 128' and correspond to current synchronized image frames thereof. Simultaneously, lights of respective wavelengths as reflected by transverse areas 124 and 126 of the surface 111 are respectively sensed by the cameras 128 and 128', corresponding to the same current synchronized frames. In a same way, illuminated transverse areas 124' and 126' of the surface 111' are sensed, corresponding also to the same current synchronized image frames. Upon displacement of the article 104, the cameras 128 and 128' generate successive image frames of image pixels, which frames correspond to a plurality of successive cross-section an associated profile traces 110 spaced in a parallel relationship along the surfaces 111 and 111' of the article 104. Furthermore, for defect detecting requiring color analysis, the successive frames correspond also to a plurality of illuminated areas as described before.

Turning now to FIG. 10, it can be seen that in an apparatus comprising four cameras 136, 136, 138 and 138' image pixel signals for each image frame are sent to respective data acquisition and pre-processing units 154, which, as mentioned before, perform selection of pixel signals related to profile traces and illuminated areas only, using conventional image threshold processing techniques well known in the art. The DSP unit 161 performs all calculation and defect detection from selected pixel signals for each image frame. More specifically, the DSP unit 161 receives the selected pixel signals, which give pixel position and intensity values. It is pointed out that the apparatus is properly calibrated to provide accurate image intensity, through an illumination calibration procedure carried out prior operation, which consists essentially in obtaining image pixel signals for a reference object showing uniform reflectivity characteristics. Light variation compensation factors are derived and used by the DSP unit 161 to normalize the pixel signals accordingly. Furthermore, dimensional calibration is performed to provide accurate derivation of dimension related parameters such as position and size of defects. Using measurement standards, the ratio dimension/pixel for both thickness and width of the object is derived as well as a position compensation factor to correct for variation on position of the cameras with respect to the central horizontal plane 132 as shown in FIG. 9. Further calculations are performed by the DSP to correct article feeding angle deviation from a direction parallel to the plane formed by opposed cameras 128 and 128', the lasers 108 and 108' and the light source units 112 and 112'. Furthermore, the number of frames between illuminated areas and the profile line as formed by the laser beam is determined. Returning to FIG. 10, after pre-processing and compensation, profile data are then derived by the DSP unit 161 from selected pixel signals using a conventional triangulation-based ranging technique. As well known in the art, ranging through triangulation calculation is essentially based on the principle that there is a direct relationship between distance separating a reference plane and a given point of the surface as measured along an axis extending in a direction perpendicular to the surface, and reflected light beam shift from a corresponding reference position as observed at the sensor location. Therefore, following proper calibration, profile data as defined by series of calculated distance values for corresponding points of the surface, can be directly derived from light beam shifts measurements. Various optical ranging methods can be used according to the present invention, as those summarized in "Active optical range imaging sensors" by Paul J. Besl, Machine Vision and Applications, pp. 127–152, which is incorporated herein by reference. The resulting profile trace data corresponds to a plurality of successive cross-sections and associated profile traces 110 and 110' spaced in a parallel relationship respectively along the surfaces 111 and 111' of the article 104. Then, as explained before with reference to FIGS. 1 and 2, from generally regular portions of the profile trace data, the DSP 161 derives through curve fitting calculation base reference curves data characterizing general orientation and position of the profile traces in relation to a reference system, which can be chosen as the central plane 132 shown in FIG. 9. Then, for each image frame, the DSP unit 161 as part of a defect detecting device compares the trace data with the base reference curve to recognize a defect induced departure of the trace data with respect to the base reference curve and to produce an output signal indicative of a surface defect such as roughness, cavity, wane, missing wood in lumber and longitudinal defect, as described before with reference to FIGS. 3 to 7. The defect threshold lines data are shifted inwardly with respect to the base reference lines data by a predetermined threshold value corresponding to the type of defect involved. For each image frame, the DSP unit 161 sends corresponding processed data to the computer 162 as part of the defect detecting device, which compares and classifies data corresponding to a plurality of successive frames to produce the output signal indicative of a defect present along one or more of the profile traces. Furthermore, since pixels positions are accurately known, the electric signal may be indicative of position of the defect along the profile traces, and along the article surface. As mentioned before, in a particular case where a wooden article is being inspected, certain types of defects such as altered wood require color analysis in combination with roughness or cavity detection. Therefore, the reflectance data comprised in the pixel signals generated by the cameras 136, 136', 138, 138' is used by the DSP to produce for each image frame, a color signal indicative of a color characteristic of the surface under inspection at the position of the detected defect is sent to the computer 161, so that altered wood is detected whenever the color signal satisfies a second specific condition, in addition to a detection of roughness or cavity related defect at this position. More specifically, the cameras 136, 136', 138 and 138', which receive reflected light from a respective article surface 144, produce reflectance data representing reflected light intensities at a pair of wavelengths. The DSP unit 161 derive a resulting difference between the reflected light intensities to produce the color signal. While the resulting difference may be expressed as a subtraction of the reflectance data for both wavelengths, this difference is preferably expressed as a ratio of the reflectance data for the pair of wavelengths. The computer applies the second specific condition that is satisfied whenever value of the color signal is higher than a predetermined color threshold value.

Figure 13:
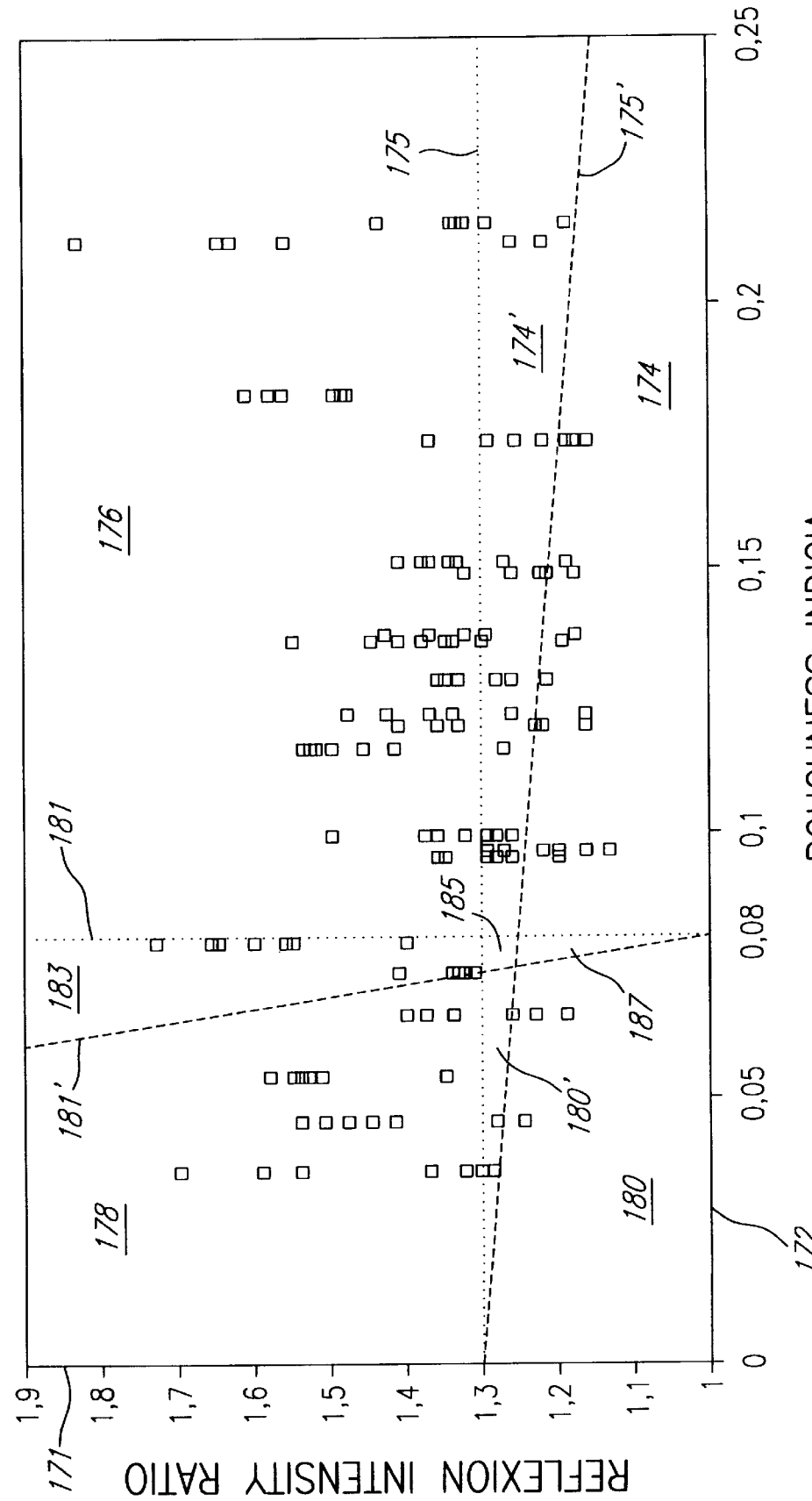
FIG. 13 is a plot of reflectivity ratio on the Y axis for measurements at two distinct wavelengths, in relation to roughness measurement, showing classification of a set of lumber pieces into three defect categories and two sound lumber categories.

Turning now to FIG. 13, there is shown a plot of reflectivity ratio on the Y axis 171 for measurements at two distinct wavelengths, which were chosen comprised within red and green portions of the visible spectrum in the example as shown in FIG. 13, in relation to roughness indicia values on the X axis 172. It is to be understood that any suitable pair of wavelengths associated with distinct portions of the visible spectrum, such as red/blue, red/yellow can be selected, provided proper light sources are available. For the purposes of the example shown in FIG. 13, LEDs arrays emitting in the red and green portions of the visible spectrum were used, which LEDs arrays are readily available on the marketplace. It can be seen that the second specific condition for detecting altered wood is satisfied whenever the reflectance ratio is higher than a predetermined threshold value as indicated by the dotted threshold line 175, which threshold value was set to 1.3 in the example shown in FIG. 13. However, the threshold value can be a function of corresponding roughness indicia value on the X axis 172, as indicated by the dotted threshold line 175', whose parameters can be selected from experimental results. It can be seen from FIG. 11 that the roughness indicia threshold value was set to a value of 0.08 according to the dotted threshold line 181. However, this threshold value can be a function of corresponding reflectance ratio values on the Y axis 171, as indicated by the dotted threshold line 181', whose parameters can be also selected from experimental results. It can be further seen that a particular one of a set of lumber pieces can be classified according to two defect categories, namely roughness 174, 174' and altered wood 176, and two sound lumber categories, namely colored wood 178, 183 and faint wood 180, 180', 185, 187 using the threshold lines 175 and 181. In a similar manner, using the threshold lines 175' and 181', roughness is identified at numeral 174, 187 altered wood at 176, 174', 183, 185 colored wood at 178, 180' and faint wood at 180. It can be seen from the graph shown in FIG. 11 that roughness indicia is essential to discriminate between colored wood and altered wood, since their respective reflectance ratio varies roughly in a same range. It is pointed out that cavity defect measurement can be also used on the X axis to provided proper classification. It is further pointed out that the computer 161 may select elements of the profile data that satisfy the first specific condition a predetermined number of times for a corresponding number of successive profile traces associated with the image frames, thereby improving defects discrimination capability. All predetermined threshold values mentioned above, such as curve fitting, color, roughness and cavity threshold values can be set through a user interface provided on the computer 161. It is to be understood that other surface characteristics such as article opposed surfaces spacing can be detected or monitored using the present invention. Advanced defect analysis can be performed by the computer for providing classification, such as derivation of ratio of defective or colored portions on total width of any profile trace, size of defects and different classification threshold values for specific parts of the article such as ends. For instance, these classification parameters may be set as desired according to classification rules as drafted by National Lumber Grading Association (NLGA). It is also understood that any obvious modification or application of the apparatus and method as described in the present specification is part of the present invention, provided it falls within the scope of the appended claims.

What is claimed is:

1. An apparatus for detecting surface defects on an article being conveyed in a scanning direction, the apparatus comprising:

surface shape inspection means for obtaining profile data of at least one surface of said article at a cross-section, said profile data being referenced to a reference system;

data processing means for deriving a base reference curve through a curve fitting algorithm applied to generally regular portions of said profile data; and defect detecting means comparing said profile data with said base reference curve to recognize a defect induced departure of said data with respect to said base reference curve and to produce a defect output signal.

2. The apparatus as claimed in claim 1, wherein said base reference curve is a straight line.

3. The apparatus as claimed in claim 1, wherein said data processing means store characteristic information about said base reference curve upstream from said cross-section to predict said base reference curve without relying exclusively on said profile data for said cross-section.

4. The apparatus as claimed in claim 1, wherein said defect detecting means compare said profile data with said base reference curve using a defect threshold curve being shifted inwardly with respect to the base reference curve by a predetermined threshold value, to select elements of the profile data which satisfy a first specific condition.

5. The apparatus as claimed in claim 4, wherein said detected defect is characterized by roughness of said at least one surface, said first specific condition being satisfied whenever the selected elements of said profile data are substantially outwardly over said defect threshold curve, said defect output signal being produced whenever:

$$\frac{\sum_{i=1}^{n} |x_i - x_{i+1}|}{n} \geq R$$

wherein:

$x_i$ represents departure value of a selected data element i among selected data elements of said profile data from the base reference curve, with i=1,n;

n is a total number of said selected elements; and

R is a predetermined roughness threshold value.

6. The apparatus as claimed in claim 4, wherein said article is a wooden article, said defect output signal being further indicative of position of said detected defect referenced to said profile data, said apparatus further comprising color sensing means for producing a color signal indicative of a color characteristic of said at least one surface at the position of said detected defect, said detected defect being further characterized by altered wood whenever said color signal satisfies a second specific condition.

7. The apparatus as claimed in claim 6, wherein said color sensing means comprises an illumination source for directing a light output onto said at least one surface, said light output comprising a pair of wavelengths, light sensing means receiving reflected light from said at least one surface to produce reflectance data representing reflected light intensities at said pair of wavelengths, means for deriving a resulting difference between said reflected light intensities to produce said color signal, said second specific condition being satisfied whenever said color signal has a value being higher than a predetermined color threshold value.

8. The apparatus as claimed in claim 7, wherein said light sensing means are at least one camera respectively associated with said at least one surface.

9. The apparatus as claimed in claim 4, wherein said detected defect is characterized by a cavity on said at least one surface, said first specific condition being satisfied whenever said profile data are substantially inwardly under said defect threshold curve.

10. The apparatus as claimed in claim 9, wherein said article is a wooden article, said defect output signal is further indicative of position of said detected defect referenced to said profile data, said apparatus further comprising color sensing means for producing a color signal indicative of a color characteristic of said at least one surface at the position of said detected defect, said detected defect being further characterized by altered wood whenever said color signal satisfies a second specific condition.

11. The apparatus as claimed in claim 10, wherein said second specific condition is satisfied whenever said color signal has a value being higher than a predetermined color threshold value.

12. The apparatus as claimed in claim 10, wherein said color sensing means comprise an illumination source for directing a light output comprising a pair of wavelengths onto said at least one surface, light sensing means receiving reflected light from said at least one surface to produce color data representing reflected light intensities at said pair of wavelengths, means for deriving a resulting difference between said reflected light intensities to produce said color signal.

13. The apparatus as claimed in claim 12, wherein said light sensing means are at least one camera respectively associated with said at least one surface.

14. The apparatus as claimed in claim 4, wherein said detected defect is characterized by a cavity on said at least one surface, said first specific condition being satisfied whenever the selected elements of said profile data are substantially inwardly under said defect threshold curve, said defect output signal being produced whenever a total number of said selected elements is higher that a predetermined cavity threshold value.

15. The apparatus as claimed in claim 4, wherein said article is a lumber piece, said detected defect being characterized by wane defined by said at least one surface, said first specific condition being satisfied whenever the selected elements of said profile data being substantially inwardly under said defect threshold curve and being associated with external end portions of said profile data, said defect output signal being produced whenever a total number of said selected elements is higher that a predetermined wane threshold value.

16. The apparatus as claimed in claim 1, wherein said means for generating profile data comprise a substantially monochromatic light emitting means for directing a beam of light at a first angle onto said at least one surface, image sensing means receiving at a second angle reflected light from said at least one surface to produce image signals representing deviation of said reflected light toward said sensing means, means to derive the profile data from said image signal through triangulation calculation of range between said at least one surface and the image sensing means.

17. The apparatus as claimed in claim 16, wherein said light emitting means comprise at least one laser source respectively associated with said at least one surface, said image sensing means comprising at least one camera respectively associated with said at least one surface.

18. An apparatus for detecting missing wood on at least one surface of a wooden article having at least one pair of opposed surfaces, said article being conveyed in a scanning direction, the apparatus comprising:

surface shape inspection means for obtaining profile data of said at least one pair of opposed surfaces at a cross-section, said profile data being referenced to a reference system;

data processing means for deriving at least a pair of base reference curves through a curve fitting algorithm applied to generally regular portions of said profile data; and missing wood detecting means for measuring spacing between said pair of base reference curves to recognize a defect induced spacing departure from a predetermined minimum spacing to produce a defect output signal.

19. The apparatus as claimed in claim 18, wherein said base reference curves are straight lines.

20. The apparatus as claimed in claim 18, wherein said data processing means store characteristic information about said base reference curves upstream from said cross-section to predict said base reference curves without relying exclusively on said profile data for said cross-section.

21. An apparatus for detecting longitudinal surface defects on an article being conveyed in a scanning direction, the apparatus comprising:

surface shape inspection means for obtaining profile data of at least one surface of said article at successive cross-sections, said profile data being referenced to a reference system;

data processing means for deriving a plurality of successive base reference curves from generally regular portions of said profile data; and defect detecting means comparing adjacent ones of said base reference curves to recognize position shifts for corresponding adjacent ones of said cross-sections and to produce a defect output signal indicative of a surface defect extending along said surface whenever values of said position shifts are higher than a predetermined defect threshold value.

22. An apparatus for detecting surface defects on an article, the apparatus comprising:

surface shape inspection means for obtaining profile data of at least one surface at successive cross-sections, said profile data being referenced to a reference system, said surface shape inspection means being displaceable with respect to said at least one surface in a scanning direction;

data processing means for deriving successive base reference curves through a curve fitting algorithm applied to generally regular portions of said profile data; and defect detecting means comparing said profile data with said successive base reference curves to recognize a defect induced departure of said data with respect to said base reference curves and to produce a defect output signal.

23. The apparatus as claimed in claim 21 or 22, wherein said base reference curves are straight lines.

24. The apparatus as claimed in claim 21 or 22, wherein said analyzer means store characteristic information about each of said base reference curves upstream from a corresponding one of said cross-section to predict each of said base reference curves without relying exclusively on said profile data for each of said cross-sections.

25. The apparatus as claimed in claim 22, wherein said defect detecting means compare said profile data with said base reference curves using corresponding defect threshold curves being shifter inwardly with respect to the base reference curves by a predetermined threshold value, to select elements of the profile data which satisfy a first specific condition.

26. The apparatus as claimed in claim 25, wherein said defect output signal is further indicative of defect position referenced to said profile data, said apparatus further comprising color sensing means for producing color data indicative of a color characteristic of said at least one surface at the position of the detected surface defect, said detected defect being characterized by altered wood whenever said color data have values being higher than a predetermined threshold value.

27. The apparatus as claimed in claim 25, wherein said first specific condition is satisfied whenever the selected elements of said profile data are substantially outwardly over said defect threshold curves, said defect output signal being produced whenever:

$$\frac{\sum_{i=1}^{n_j} |x_i - x_{i+1}|}{n_j} \geq R$$

wherein:

$X_{i,j}$ represents departure value of a selected data element i among selected data elements of said profile data from the base reference curve value for a cross-section j of said successive cross-sections, with i=1,$n_j$ and j=1,m;

$n_j$ is a total number of said selected elements for said cross-section j;

m is the number of said successive cross-section; and

R is a predetermined roughness threshold value.

28. The apparatus as claimed in claim 25, wherein said detected defect is characterized by a cavity on said at least one surface, said first specific condition being satisfied whenever the selected elements are substantially inwardly under the corresponding defect threshold curves, said defect signal being produced whenever a total number of said selected elements is higher than a predetermined cavity threshold value.

29. The apparatus as claimed in claim 25, wherein said first specific condition is satisfied whenever the selected elements of said profile data are substantially inwardly under the corresponding defect threshold curves and are associated with external end portions of said cross-sections, said defect signal being produced whenever a total number of said selected elements is higher that a predetermined wane threshold value.

30. A method for detecting surface defects on an article the method comprising steps of:

i) obtaining profile data of at least one surface of said article at a cross-section, said profile data being reference to a reference system;

ii) deriving a base reference curve through a curve fitting algorithm applied to generally regular portions of said profile data:

iii) comparing said profile data with said base reference curve to recognize a defect induced departure of said profile data with respect to said base reference curve; and iv) producing a defect output signal.

31. The method as claimed in claim 30, wherein said step (ii) comprises steps of:

a) defining an initial reference curve corresponding to said cross-section;

b) defining a first threshold curve shifted with respect to the initial reference curve by a predetermined threshold value;

c) selecting elements of the profile data which have values higher than said threshold curve;

d) applying a curve fitting calculation to derive said base reference curve;

e) repeating the steps a) to d) to derive a following base reference curve corresponding to a following cross-section in a scanning direction.

32. The method as claimed in claim 30, wherein said base reference curve is a straight line.

33. The method as claimed in claim 30, wherein said step ii) is performed by storing characteristic information about said base reference curve upstream from said cross-section to predict said base reference curve without relying exclusively on said profile data for said cross-section.

34. The method as claimed in claim 30, wherein said step iii) is performed using a defect threshold curve being shifted inwardly with respect to the base reference curve by a predetermined threshold value to select elements of the profile data which satisfy a first specific condition.

35. The method as claimed in claim 34, wherein said detected defect is characterized by roughness of said at least one surface, said first specific condition being satisfied whenever the selected elements of said profile data are substantially over said defect threshold curve, said defect output signal being produced whenever:

$$\frac{\sum_{i=1}^{n} |x_i - x_{i+1}|}{n} \geq R \tag{3}$$

wherein:

$X_i$ represents value of a selected data element i among selected data elements of said profile data, with i=1,n;

n is a total number of said selected elements; and

R is a predetermined roughness threshold value.

36. The method as claimed in claim 34, wherein said detected surface defect is characterized by a cavity on said at least one surface, said first specific condition being satisfied whenever said profile data are substantially inwardly under said defect threshold curve.

37. The method as claimed in claim 34, wherein said detected surface defect is characterized by a cavity on said at least one surface, said first specific condition being satisfied whenever the selected elements of said profile data are substantially inwardly under the defect threshold curve, said defect signal being produced whenever a total number of said selected elements is higher than a predetermined cavity threshold value.

38. The method as claimed in claim 34, wherein said detected surface defect being characterized by wane defined by said at least one surface, said first specific condition being satisfied whenever the selected elements of said profile data are substantially inwardly under the defect threshold curve and are associated with external end portions of said cross-section, said defect signal being produced whenever a total number of said selected elements is higher that a predetermined wane threshold value.

39. A method for detecting missing wood on at least one surface of a wooden article having at least one pair of opposed surfaces, comprising steps of:
  i) generating profile data of said at least one pair of opposed surfaces at a cross-section, said profile data being referenced to a reference system;
  ii) deriving at least a pair of base reference curves through a curve fitting algorithm applied to generally regular portions of said profile data;
  iii) measuring spacing between said pair of base reference curves to recognize a defect induced spacing departure from a predetermined minimum spacing; and
  iv) producing a defect output signal.

40. A method for detecting longitudinal surface defects on an article comprising steps of:
  i) generating profile data of at least one surface of said article at successive cross-sections, said profile data being referenced to a reference system;
  ii) deriving a plurality of successive base reference curves from generally regular portions of said profile data;
  iii) comparing adjacent ones of said base reference curves to recognize position shifts for corresponding adjacent ones of said cross-sections;
  iv) producing a defect output signal indicative of a surface defect extending along said surface whenever values of said position shifts are higher than a predetermined defect threshold value.

* * * * *

UNITED STATES PATENT AND TRADEMARK OFFICE
CERTIFICATE OF CORRECTION

PATENT NO. : 6,122,065
DATED : September 19, 2000
INVENTOR(S) : Pierre Gauthier

It is certified that error appears in the above-identified patent and that said Letters Patent is hereby corrected as shown below:

Column 7,
Line 12, before "the" insert -- with --.

Column 8,
Line 20, symbol "66" should read -- $\Delta$ --;
Line 21, "with" should read -- to --;
Line 23, cancel "trace";
Line 25, before "under" insert -- inwardly --;
Line 26, "to" should read -- with --;
Line 41, "process" should read -- processed --;
Line 50, cancel "trace";
Line 54, "trace" should read -- profile --;
Lines 57 and 61, "shift data", each occurrence, should read -- shifts --; same line 61, "is" should read -- are --.

Column 12,
Line 11, "237" should read -- 234 --;
Line 12, "237'" should read -- 234' --;
Lines 18, 19, 20 and 24, "234", each occurrence, should read -- 237 --; same line 24, "238'" should read -- 239 --; and "238'" should read -- 239' --;
Line 22, "239'" should read -- 238 --;
Lines 28 and 30, "238" and "238'", each occurrence, should read -- 239 -- and -- 239' --, respectively;
Line 67, cancel "trace".

Column 13,
Line 12, "208" should read -- 242 --;
Line 62, "136, 136" should read -- 136, 136' --.

Column 14,
Lines 43 and 49, "trace", each occurrence, should read -- profile --;
Lines 55 and 56, "trace", each occurrence, should read -- profile --.

UNITED STATES PATENT AND TRADEMARK OFFICE
CERTIFICATE OF CORRECTION

PATENT NO. : 6,122,065
DATED : September 19, 2000
INVENTOR(S) : Pierre Gauthier

It is certified that error appears in the above-identified patent and that said Letters Patent is hereby corrected as shown below:

Column 15,
Line 10, "136, 136" should read -- 136, 136' --;
Lines 50 and 65, "Fig. 11" each occurrence, should read -- Fig. 13 --.

Claim 35,
Line 52, before "over" insert -- outwardly --.

Signed and Sealed this

Twenty-ninth Day of January, 2002

Attest:

Attesting Officer

JAMES E. ROGAN
Director of the United States Patent and Trademark Office